United States Patent
Shimokawa et al.

(10) Patent No.: US 10,772,882 B2
(45) Date of Patent: Sep. 15, 2020

(54) PULMONARY HYPERTENSION PREVENTATIVE OR THERAPEUTIC AGENT CONTAINING CRUDE DRUG

(71) Applicant: TOHOKU UNIVERSITY, Miyagi (JP)

(72) Inventors: Hiroaki Shimokawa, Miyagi (JP); Hidetoshi Tokuyama, Miyagi (JP); Hirofumi Ueda, Miyagi (JP); Jyunken Aoki, Miyagi (JP); Takayuki Doi, Miyagi (JP); Kuniyuki Kano, Miyagi (JP); Kimio Satoh, Miyagi (JP); Ryo Kurosawa, Miyagi (JP)

(73) Assignee: TOHOKU UNIVERSITY, Miyagi (JP)

( * ) Notice: Subject to any disclaimer, the term of this patent is extended or adjusted under 35 U.S.C. 154(b) by 0 days.

(21) Appl. No.: 16/310,209

(22) PCT Filed: Mar. 28, 2017

(86) PCT No.: PCT/JP2017/012717
§ 371 (c)(1),
(2) Date: Dec. 14, 2018

(87) PCT Pub. No.: WO2017/217072
PCT Pub. Date: Dec. 21, 2017

(65) Prior Publication Data
US 2019/0321354 A1  Oct. 24, 2019

(30) Foreign Application Priority Data
Jun. 17, 2016  (JP) .................. 2016-120901

(51) Int. Cl.
*A61K 31/4745* (2006.01)
*A61P 9/12* (2006.01)

(52) U.S. Cl.
CPC ............ *A61K 31/4745* (2013.01); *A61P 9/12* (2018.01)

(58) Field of Classification Search
CPC ........ A61K 31/33; A61K 31/4745; A61P 9/12
See application file for complete search history.

(56) References Cited

FOREIGN PATENT DOCUMENTS

| JP | 2016-56115 | 4/2016 |
|---|---|---|
| KR | 10-2014-0046808 | 4/2014 |

OTHER PUBLICATIONS

Nicollini, Pietro-Maria A contribution to the pharmacologic study of emetine Archives Internationales de Pharmacodynamie et de Therapie (1923), 28, 61-73. abstarct.*

International Search Report dated May 9, 2017 in International (PCT) Application No. PCT/JP2017/012717.
Kazufumi Nakamura et al., "Characteristics of pulmonary artery smooth muscle cells and endothelial cells in IPAH", Journal of Clinical and Experimental Medicine (separate volume), Hai Koketsuatsu Shindan no Shinpo, Dec. 2012, pp. 36-40, with partial English translation.
Noritsugu Tohse, "Alternation of regulation system for pulmonary arterial tone in pulmonary hypertension", The Japanese Journal of Clinical Medicine, Jun. 2001, vol. 59, pp. 1065-1069, with English abstract.
Kiyoko Takemiya et al., "Gene cell therapy for idiopathic pulmonary arterial hypertension", The Japanese Journal of Clinical Medicine, Nov. 2008, vol. 66, No. 11, pp. 2187-2192, with English abstract.
D.J. Miletich et al., "The effect of emetine on myocardial catecholamine metabolism", Journal of Pharmacy and Pharmacology, 1974, vol. 26, pp. 101-104.
Japanese Journal of Clinical Medicine (separate volume) Ryoiki Betsu Shokogun Series 36 Kokkakukin shokogun (last volume) Sep. 2001, pp. 247-249, cited in ISR.
Kuchuyaku, Yakurigaku (Hirokawa Shoten), 1st edition, Feb. 1992, pp. 439-452, cited in ISR.
Saitoyaku Emetics, Japanese Journal of Clinical Medicine (special extra issue) Saishin Yakubutsu Ryoho manual (fist volume), Jun. 1991, vol. 49, No. 622, pp. 268-269, cited in ISR.
Marlene Rabinovitch, "Molecular pathogenesis of pulmonary arterial hypertension", The Journal of Clinical Investigation, Dec. 2012, vol. 122, No. 12, pp. 4306-4313.
Toby L. Litovitz et al., 1996 Annual Report of the American Association of Poison Control Centers Toxic Exposure Surveillance Systems, American Journal of Emergency Medicine, Sep. 1997, vol. 15, No. 5, pp. 447-500.
Kimberly E. Foreman et al., "Emetine Dihydrochloride: A Novel Therapy for Bladder Cancer", The Journal of Urology, Feb. 2014, vol. 191, No. 2, pp. 502-509.
Susanne C. Miller et al., "Identification of known drugs that act as inhibitors of NF-κB signaling and their mechanism of action", Biochemical Pharmacology, May 2010, vol. 79, No. 9, pp. 1272-1280.
S. Hosokaw et al., "Novel Selective Nfκb Inhibitor Compound Suppresses Pulmonary Arterial Smooth Muscle Cell Proliferation for Pulmonary Arterial Hypertension", American Thoracic Society International Conference Abstracts, 2012, B63, A3406.

* cited by examiner

*Primary Examiner* — Jennifer M Kim
(74) *Attorney, Agent, or Firm* — Wenderoth, Lind & Ponack, L.L.P.

(57) ABSTRACT

A problem to be solved by the present invention is to provide a novel preventive or therapeutic agent for pulmonary hypertension containing as an active ingredient a compound that has not been known for a therapeutic effect on pulmonary hypertension heretofore. The present invention provides a preventive or therapeutic agent for pulmonary hypertension containing emetine or a salt thereof.

8 Claims, 2 Drawing Sheets

PULMONARY HYPERTENSION PREVENTATIVE OR THERAPEUTIC AGENT CONTAINING CRUDE DRUG

TECHNICAL FIELD

Cross Reference to Related Application

The present application claims priority from Japanese Patent Application No. 2016-120901 filed on Jun. 17, 2016, the disclosure of which is incorporated herein by reference in its entirety. The present invention relates to a preventive or therapeutic agent for pulmonary hypertension.

BACKGROUND ART

Pulmonary hypertension is a disease involving increased blood pressure in pulmonary arteries, which carry blood from heart to lungs, leading to impaired cardiac and pulmonary functions, and is a disease quite different from a symptom generally called "hypertension". In addition, pulmonary hypertension is a severe disease with high lethality, and hence there is an urgent need to develop a therapeutic method therefor.

Conventional treatments for pulmonary hypertension include vasodilation treatment using a catheter, and treatment such as surgical removal of thrombus, but less invasive therapeutic methods are desired. In addition, a vasodilator or the like is known as medication (e.g., Non-patent Literature 1), but there are still a large number of patients that cannot be saved by such therapeutic method. Thus, there is a strong demand for further development of a therapeutic agent for pulmonary hypertension.

CITATION LIST

Non-Patent Literature

NPL 1: J Clin Invest. 2012; 122(12): 4306-4313
NPL 2: Am J Emerg Med. 15, 447-500, 1997
NPL 3: J Urol. 2014 February; 191(2): 502-9
NPL 4: Biochem Pharmacol. 2010 May 1; 79(9): 1272-80
NPL 5: American Thoracic Society International Conference Abstracts 2012, B63, A3406

SUMMARY OF INVENTION

Technical Problem

A problem to be solved by the present invention is to provide a novel preventive or therapeutic agent for pulmonary hypertension containing as an active ingredient a compound that has not been known for a therapeutic effect on pulmonary hypertension heretofore.

Solution to Problem

Under such circumstances, the inventors of the present invention have investigated thousands of kinds of compounds. As a result, the inventors have found that emetine serving as a crude drug ingredient suppresses excessive proliferation of pulmonary artery smooth muscle cells, which is said to be one of the causes for pulmonary hypertension, and has a preventive or therapeutic effect on pulmonary hypertension. The present invention is based on such novel findings.

Thus, the present invention provides the following items:

Item 1. A preventive or therapeutic agent for pulmonary hypertension, including emetine or a salt thereof.

Item 2. A preventive or therapeutic agent for pulmonary hypertension according to Item 1, wherein a daily dose of the preventive or therapeutic agent for pulmonary hypertension is 8 mg or less in terms of dose of emetine.

Item 3. A preventive or therapeutic agent for pulmonary hypertension according to Item 1 or 2, wherein the preventive or therapeutic agent for pulmonary hypertension is an orally administered agent.

Item 4-1. A method of preventing or treating pulmonary hypertension, including administering an effective dose of emetine or a salt thereof.

Item 4-2. A method according to Item 4-1, wherein a daily dose of the emetine or the salt thereof is 8 mg or less in terms of dose of emetine.

Item 4-3. A method according to Item 4-1 or 4-2, wherein the administering includes orally administering the emetine or the salt thereof.

Item 5-1. Emetine or a salt thereof, for use in prevention or treatment of pulmonary hypertension.

Item 5-2. Emetine or a salt thereof according to Item 5-1, wherein a daily dose of the emetine or the salt thereof is 8 mg or less in terms of dose of emetine.

Item 5-3. Emetine or a salt thereof according to Item 5-1 or 5-2, wherein the prevention or treatment of pulmonary hypertension is performed by orally administering the emetine or the salt thereof.

Item 6-1. A use of emetine or a salt thereof, for manufacture of a preventive or therapeutic agent for pulmonary hypertension.

Item 6-2. A use according to Item 6-1, wherein a daily dose of the preventive or therapeutic agent for pulmonary hypertension is 8 mg or less in terms of dose of emetine.

Item 6-3. A use according to Item 6-1 or 6-2, wherein the preventive or therapeutic agent for pulmonary hypertension is an orally administered agent.

Advantageous Effects of Invention

According to the present invention, the novel preventive or therapeutic agent for pulmonary hypertension can be provided by using emetine, which is a compound that has not been known for a therapeutic effect on pulmonary hypertension heretofore, or a salt thereof as an active ingredient.

In this connection, ipecac, which contains emetine serving as the active ingredient of the present invention, has a history of having been empirically used as a therapeutic drug for amebic dysentery by Brazil's indigenous people since olden times. In addition, in the past, Tsumura & Co. sold an extract of crude drug ipecac containing emetine and cephaeline, which was a metabolite of emetine, as an emetic under the product name of Ipecac Syrup, which was administered to 3,000,000 or more patients in Europe and the United States, and which was considered to be a pharmaceutical agent having high safety when used properly (Non-patent Literature 2). At present, the product has been discontinued because of its side effects such as gastrointestinal dysfunction. In addition, there is a report of an article showing the action of emetine as an anticancer drug (Non-patent Literature 3). However, there is no previous report that emetine has a preventive or therapeutic effect on pulmonary hypertension. Accordingly, the surprising effect of the present invention is unpredictable from the related art.

DESCRIPTION OF EMBODIMENTS

Figure 1:
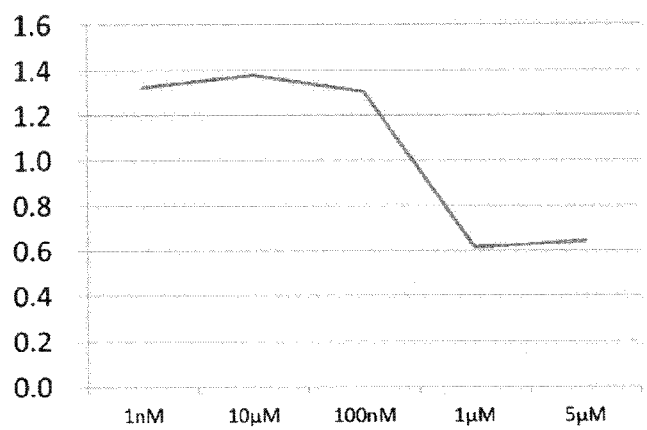
FIG. 1 is a graph for showing the results of an in vitro test in Example 1.

Preventive or Therapeutic Agent for Pulmonary Hypertension

The present invention provides a preventive or therapeutic agent for pulmonary hypertension containing emetine or a salt thereof. Emetine [CAS No. 483-18-1, (2S,3R,11bS)-2-(((R)-6,7-dimethoxy-1,2,3,4-tetrahydroisoquinolin-1-yl)methyl)-3-ethyl-9,10-dimethoxy-3-methyl-1,3,4,6,7,11b-hexahydro-2H-pyrido[2,1-a]isoquinoline] serving as an active ingredient of the present invention is a known substance having the following structure:

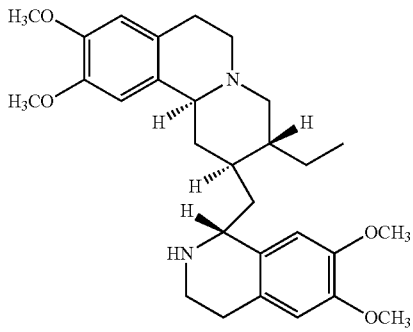 [SMILES: CC[C@H]1CN2CCc3cc(OC)c(OC)cc3[C@@H]2C[C@@H]1C[C@H]1NCCc2cc(OC)c(OC)cc21]

The salt of emetine serving as the active ingredient of the present invention encompasses an acid addition salt and a salt with a base. Specific examples of the acid addition salt include: inorganic acid salts, such as a hydrochloride, a hydrobromide, a hydroiodide, a sulfate, a perchlorate, and a phosphate; organic acid salts, such as an oxalate, a malonate, a succinate, a maleate, a fumarate, a lactate, a malate, a citrate, a tartrate, a benzoate, a trifluoroacetate, an acetate, a methanesulfonate, a p-toluenesulfonate, and a trifluoromethanesulfonate; and acidic amino acid salts, such as a glutamate and an aspartate. Specific examples of the salt with a base include: alkali metal or alkaline earth metal salts, such as a sodium salt, a potassium salt, and a calcium salt; salts with organic bases, such as a pyridine salt and a triethylamine salt; and salts with basic amino acids, such as lysine and arginine.

Emetine and the salt thereof serving as the active ingredient of the present invention may be present in the form of a hydrate or a solvate, and hence the compound serving as the active ingredient of the present invention also encompasses such hydrate and solvate.

A solvent forming the solvate is exemplified by alcohols, such as ethanol and propanol, organic acids, such as acetic acid, esters, such as ethyl acetate, ethers, such as tetrahydrofuran and diethyl ether, ketones, such as acetone, and DMSO. Those solvents may be used alone or as a mixed solvent thereof.

In the present invention, emetine or the salt thereof serving as the active ingredient of the present invention may be used alone as a preventive or therapeutic agent for pulmonary hypertension, or may be used as a pharmaceutical composition in combination with any of various pharmaceutically acceptable carriers (e.g., a tonicity agent, a chelating agent, a stabilizing agent, a pH regulator, a preservative, an antioxidant, a solubilizing agent, or a thickening agent).

Examples of the tonicity agent include: sugars, such as glucose, trehalose, lactose, fructose, mannitol, xylitol, and sorbitol; polyhydric alcohols, such as glycerol, polyethylene glycol, and propylene glycol; and inorganic salts, such as sodium chloride, potassium chloride, and calcium chloride. Those tonicity agents may be used alone or in combination thereof.

Examples of the chelating agent include: edentates, such as disodium edetate, calcium disodium edetate, trisodium edetate, tetrasodium edetate, and calcium edetate; ethylenediaminetetraacetate; nitrilotriacetic acid or salts thereof; sodium hexametaphosphate; and citric acid. Those chelating agents may be used alone or in combination thereof.

An example of the stabilizing agent is sodium hydrogen sulfite.

Examples of the pH regulator include acids, such as hydrochloric acid, carbonic acid, acetic acid, and citric acid, and also include: alkali metal hydroxides, such as sodium hydroxide and potassium hydroxide; alkali metal carbonates or hydrogen carbonates, such as sodium carbonate; alkali metal acetates, such as sodium acetate; alkali metal citrates, such as sodium citrate; and bases, such as trometamol. Those pH regulators may be used alone or in combination thereof.

Examples of the preservative include: sorbic acid; potassium sorbate; parahydroxybenzoates, such as methyl parahydroxybenzoate, ethyl parahydroxybenzoate, propyl parahydroxybenzoate, and butyl parahydroxybenzoate; quaternary ammonium salts, such as chlorhexidine gluconate, benzalkonium chloride, benzethonium chloride, and cetylpyridinium chloride; alkylpolyaminoethylglycine; chlorobutanol; polyquad; polyhexamethylene biguanide; and chlorhexidine. Those preservatives may be used alone or in combination thereof.

Examples of the antioxidant include sodium hydrogen sulfite, dried sodium sulfite, sodium pyrosulfite, and concentrated mixed tocopherols. Those antioxidants may be used alone or in combination thereof.

Examples of the solubilizing agent include sodium benzoate, glycerin, D-sorbitol, glucose, propylene glycol, hydroxypropyl methylcellulose, polyvinylpyrrolidone, macrogol, and D-mannitol. Those solubilizing agents may be used alone or in combination thereof.

Examples of the thickening agent include polyethylene glycol, methyl cellulose, ethyl cellulose, carmellose sodium, xanthan gum, sodium chondroitin sulfate, hydroxyethyl cellulose, hydroxypropyl cellulose, hydroxypropyl methylcellulose, polyvinylpyrrolidone, and polyvinyl alcohol. Those thickening agents may be used alone or in combination thereof.

In addition, the pharmaceutical composition may further contain, in addition to emetine or the salt thereof, a compound known to have a preventive or therapeutic action on pulmonary hypertension. Examples of the compound known to have a preventive or therapeutic action on pulmonary hypertension include a prostacyclin preparation (e.g., epoprostenol), a PDE5 inhibitor (e.g., tadalafil), and an endothelin receptor antagonist (e.g., bosentan). Those compounds may be used alone or in combination thereof.

In addition, in the present invention, an extract itself of crude drug ipecac, or a composition obtained by adding any of the above-mentioned various carriers to the extract may be used as the preventive or therapeutic agent for pulmonary hypertension. Meanwhile, the preventive or therapeutic agent for pulmonary hypertension in the present invention contains emetine or a salt thereof as an active ingredient, and hence may not have blended therein cephaeline serving as an ingredient other than emetine in the extract of crude drug ipecac.

In the embodiment of the pharmaceutical composition, the content of emetine or the salt thereof in the composition is not particularly limited, and may be appropriately set within, for example, conditions such as 90 mass % or more, 70 mass % or more, 50 mass % or more, 30 mass % or more, 10 mass % or more, 5 mass % or more, and 1 mass % or more in terms of the content of emetine.

A dosage form is not particularly limited, and examples thereof may include various dosage forms including: orally administered agents, such as a tablet, a pill, a capsule, a powder, a granule, and a syrup; and parenterally administered agents, such as an injection (e.g., intravenous injection, intramuscular injection, or local injection), a gargle, a drop, external preparations (an ointment, a cream, a patch, and an inhalant), and a suppository. Of the dosage forms, for example, orally administered agents (e.g., a tablet, a pill, a capsule, a powder, a granule, and a syrup) and external preparations (e.g., an inhalant, an ointment, a cream, and a patch) are preferred.

In the present invention, the dose of emetine or the salt thereof varies depending on, for example, an administration route and the age, body weight, or symptom of a patient, and hence cannot be uniquely defined. However, the dose only needs to be such an amount that a daily dose for adults is generally about 5,000 mg or less, preferably about 1,000 mg or less in terms of the dose of emetine. In addition, according to the present invention, emetine exhibits an effect even at a low dose, and hence the dose may be, for example, such an amount that a daily dose for adults is about 100 mg or less, about 10 mg or less, about 8 mg or less, or about 5 mg or less in terms of the dose of emetine. The lower limit of the dose of emetine or the salt thereof is also not particularly limited, and may be appropriately set within, for example, such a range that a daily dose for adults is generally 0.1 mg or more, preferably 0.5 mg or more in terms of the dose of emetine. When administered once daily, emetine or the salt thereof only needs to be contained in the above-mentioned amount in a single dose. When administered three times daily, emetine or the salt thereof only needs to be contained in an amount corresponding to one-third of the above-mentioned amount in a single dose.

The preventive or therapeutic agent for pulmonary hypertension of the present invention is administered to patients, such as mammals. Examples of the mammals include humans, monkeys, mice, rats, rabbits, cats, dogs, pigs, cattle, horses, and sheep.

The preventive or therapeutic agent for pulmonary hypertension of the present invention prevents or treats and ameliorates pulmonary hypertension by at least suppressing excessive proliferation of pulmonary artery smooth muscle cells. Accordingly, the present invention also provides a suppressor for excessive proliferation of pulmonary artery smooth muscle cells containing emetine or a salt thereof. Emetine serving as the active ingredient of the present invention is known to inhibit a transcription factor NF-κB involved in, for example, embryonic and neuronal development, cell proliferation, apoptosis, immune responses, and inflammation (Non-patent Literature 4). In addition, there is a previous report that a specific compound IMD-0354 (N-[3,5-bis(trifluoromethyl)phenyl]-5-chloro-2-hydroxybenzamide) has an NF-κB-inhibiting action, suppresses the proliferation of pulmonary artery smooth muscle cells, and may have a therapeutic effect on pulmonary hypertension (Non-patent Literature 5). However, emetine serving as the active ingredient of the present invention is a compound quite different in structure from IMD-0354 described above. Further, the inventors of the present invention examined N-p-tosyl-L-phenylalanine chloromethyl ketone, caffeic acid phenethyl ester, and Nα-p-tosyl-L-lysine chloromethyl ketone hydrochloride serving as compounds known to have NF-κB-inhibiting actions for their suppressive effects on the proliferation of pulmonary artery smooth muscle cells derived from patients with pulmonary hypertension by the same method as that described in Example 1 to be described later except that each of these compounds was added so that its final concentration was 5 μM. As a result, the proliferation of the pulmonary artery smooth muscle cells was not sufficiently suppressed (data not shown). Also from such viewpoints, the suppressive effect of emetine on excessive proliferation of pulmonary artery smooth muscle cells and the preventive or therapeutic effect of emetine on pulmonary hypertension in the present invention are unpredictable from the related art. The active ingredient, dosage form, dose, and the like of the suppressor for excessive proliferation of pulmonary artery smooth muscle cells are the same as those of the preventive or therapeutic agent for pulmonary hypertension.

The present invention is more specifically described below by way of Examples. However, the present invention is not limited thereto.

EXAMPLES

Example 1

Pulmonary artery smooth muscles derived from patients with pulmonary arterial hypertension were treated with 1 nmol/L to 5 μmol/L emetine solutions (the emetine solutions were prepared with distilled water), and were cultured for 0 hours and 48 hours, followed by an MTT assay to assess cell proliferation rates. Specifically, smooth muscle cells were seeded in 96-well plates at 5,000 cells/well, and 24 hours after the seeding, emetine was added so that its final concentrations were adjusted to from 1 nmol/L to 5 μmol/L. The results are shown in FIG. 1.

As shown in FIG. 1, the results suggested that emetine suppressed proliferation of the pulmonary artery smooth muscles derived from patients with pulmonary arterial hypertension in a concentration-dependent manner.

Example 2

In vivo tests using pulmonary hypertension animal models were performed on emetine. Specifically, first, the influence of emetine on a monocrotaline-induced pulmonary hypertension model was investigated. A monocrotaline solution used for the production of the pulmonary hypertension model was prepared by dissolving monocrotaline with 1 mol/L hydrochloric acid and then adjusting the pH to 7.4 through titration with 1 mol/L sodium hydroxide using a pH meter. An emetine solution was prepared with distilled water. The monocrotaline-induced pulmonary hypertension model was produced by subcutaneously injecting 6-week-old rats (SD rats, n=13) with 60 mg/kg monocrotaline. After the subcutaneous injection with monocrotaline, the rats were orally administered 0.01 mg/kg or 0.05 mg/kg emetine daily for 3 weeks. A vehicle group was sacrificed 3 weeks after the administration of distilled water to measure right ventricular systolic pressure with Mikro-Tip Catheter transducers 2F (Millar). In addition, after formalin fixation, the right ventricle was removed from the left ventricle to measure a right ventricle/(left ventricle plus septum) weight ratio. Then, the extent of pulmonary hypertension was assessed on the basis of those results. The results are shown in FIG. 2.

Figure 2:
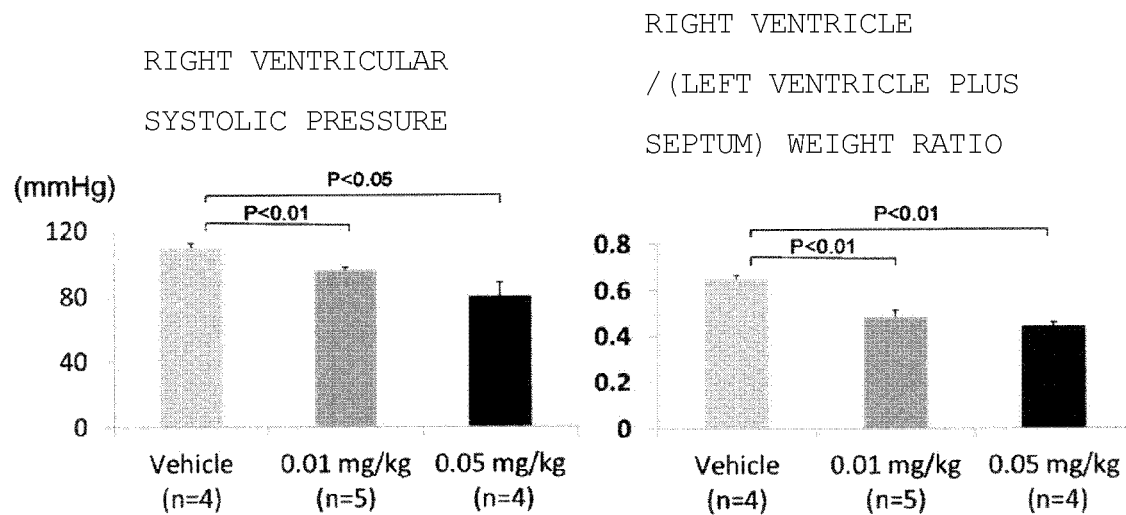
FIG. 2 are graphs for showing the influence of emetine on a monocrotaline-induced pulmonary hypertension model in Example 2.

As shown in FIG. 2, the exacerbation of the right ventricular systolic pressure and the right ventricle/(left ventricle plus septum) weight ratio was suppressed in the emetine treatment group as compared to the control group. The results suggested the suppression of the development of monocrotaline-induced pulmonary hypertension.

In addition, an in vivo test using an SU5416/Hypoxia model was also performed. Specifically, first, an SU5416 (semaxanib) solution used for the production of the model was prepared by dissolving SU5416 using carboxy methyl cellulose (CMC). An emetine solution was prepared in the same manner as described above.

Six-week-old rats (SD rats, n=9) were administered 20 mg/kg SU5416 and then bred in a hypoxic chamber using a hypoxicator to be exposed to hypoxia (oxygen concentration: from 8% to 12%) for 3 weeks and then to normoxia. Then, the rats were orally administered 0.01 mg/kg or 0.05 mg/kg emetine daily for a period from the first day of week 8 after the SU5416 administration to the final day of week 11, and were sacrificed on the final day of week 11. Then, the extent of pulmonary hypertension was assessed in the same manner as in the monocrotaline-induced pulmonary hypertension model. The results are shown in FIG. 3.

Figure 3:
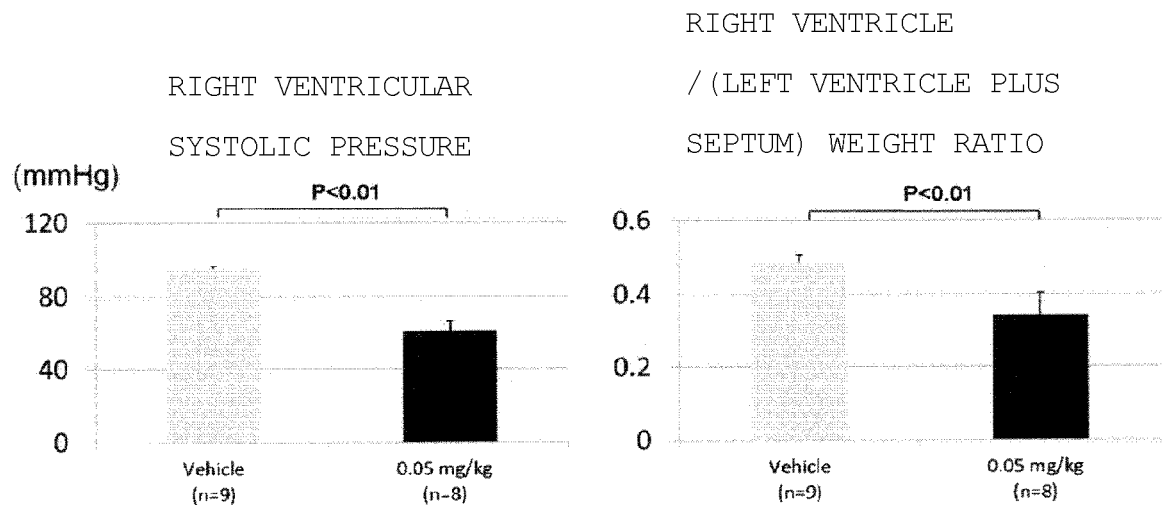
FIG. 3 are graphs for showing the influence of emetine on an SU5416/Hypoxia model in Example 2.

As shown in FIG. 3, increases in right ventricular systolic pressure and right ventricle/(left ventricle plus septum) weight ratio were alleviated in the emetine treatment group as compared to the control group. The results suggested the alleviation of SU5416/hypoxia-induced pulmonary hypertension.

The invention claimed is:

1. A method of treating pulmonary hypertension, comprising administering to a subject in need thereof an effective dose of emetine or a salt thereof.

2. The method according to claim 1, wherein a daily dose of the preventive or therapeutic agent for pulmonary hypertension is 8 mg or less in terms of dose of emetine.

3. The method according to claim 1, wherein pulmonary hypertension is pulmonary arterial hypertension.

4. The method according to claim 2, wherein pulmonary hypertension is pulmonary arterial hypertension.

5. The method according to claim 1, wherein emetine or a salt is orally administered.

6. The method according to claim 2, wherein emetine or a salt is orally administered.

7. The method according to claim 3, wherein emetine or a salt is orally administered.

8. The method according to claim 4, wherein emetine or a salt is orally administered.

* * * * *